(12) United States Patent
Mueller et al.

(10) Patent No.: US 7,214,223 B2
(45) Date of Patent: May 8, 2007

(54) PHOTOATHEROLYTIC CATHETER APPARATUS AND METHOD

(75) Inventors: Richard L. Mueller, Byron, CA (US); U. Hiram Chee, Santa Cruz, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 371 days.

(21) Appl. No.: 09/816,832

(22) Filed: Mar. 22, 2001

(65) Prior Publication Data

US 2001/0037080 A1    Nov. 1, 2001

Related U.S. Application Data

(60) Provisional application No. 60/191,777, filed on Mar. 24, 2000.

(51) Int. Cl.
*A61B 18/22* (2006.01)
*A61B 18/24* (2006.01)
*A61N 5/067* (2006.01)

(52) U.S. Cl. .............................. 606/10; 606/7; 606/15; 607/89

(58) Field of Classification Search .................. 606/7, 606/10, 15–17; 607/88, 89
See application file for complete search history.

(56) References Cited

U.S. PATENT DOCUMENTS

| | | | |
|---|---|---|---|
| 3,773,034 | A | 11/1973 | Burns et al. |
| 3,952,742 | A | 4/1976 | Taylor |
| 4,296,100 | A | 10/1981 | Franco |
| 4,531,936 | A | 7/1985 | Gordon |
| 4,657,536 | A | 4/1987 | Dorman |
| 4,770,653 | A | 9/1988 | Shturman |
| 4,911,148 | A | 3/1990 | Sosnowski et al. |
| 4,946,442 | A | 8/1990 | Sanagi |

(Continued)

FOREIGN PATENT DOCUMENTS

WO    WO 96/32129    10/1996

(Continued)

OTHER PUBLICATIONS 5,733,250, Withdrawn.

(Continued)

*Primary Examiner*—David M. Shay
(74) *Attorney, Agent, or Firm*—Jones Day

(57) ABSTRACT

A method and apparatus for treating an atherosclerotic target region of a coronary vessel in a patient are disclosed. The method includes delivering to the patient, a photoatherolytic compound, to cause accumulation of the compound in the target region, accessing the target region intraluminally with a guidewire, and advancing over the guidewire, a catheter having (i) a proximal main-body sleeve, (ii) a flexible, non-inflatable, translucent distal-end sleeve joined to the main-body sleeve at a catheter juncture, and (iii) an inner lumen extending through the two sleeves, said advancing being effective to position the catheter's distal-end sleeve within the target region. The guidewire is then removed and replaced by a fiber-optic bundle having a light-diffusing tip, until said tip is positioned adjacent the catheter juncture. After injecting a light-transmissive fluid through the catheter into the catheter's distal-end sleeve, the target vessel region is irradiated by passing a laser light beam through the fiber optic bundle.

4 Claims, 5 Drawing Sheets

U.S. PATENT DOCUMENTS

| | | | |
|---|---|---|---|
| 4,994,033 A | 2/1991 | Shockey et al. | |
| 5,019,075 A * | 5/1991 | Spears et al. | 606/7 |
| 5,041,109 A * | 8/1991 | Abela | 606/15 |
| 5,061,223 A | 10/1991 | Yock | |
| 5,185,004 A | 2/1993 | Lashinski | |
| 5,203,772 A | 4/1993 | Hammerslag et al. | |
| 5,244,460 A | 9/1993 | Unger et al. | |
| RE34,544 E * | 2/1994 | Spears | 606/7 |
| 5,385,148 A | 1/1995 | Lesh et al. | |
| 5,417,667 A * | 5/1995 | Tennican et al. | 604/191 |
| 5,419,777 A | 5/1995 | Hofling | |
| 5,445,608 A * | 8/1995 | Chen et al. | 604/20 |
| 5,489,575 A | 2/1996 | Lee et al. | |
| 5,499,971 A | 3/1996 | Shapland et al. | |
| 5,507,724 A | 4/1996 | Hofmann et al. | |
| 5,569,160 A | 10/1996 | Sauer et al. | |
| 5,569,217 A | 10/1996 | Luther | |
| 5,571,215 A | 11/1996 | Sterman et al. | |
| 5,591,195 A | 1/1997 | Taheri et al. | |
| 5,653,684 A | 8/1997 | Laptewicz et al. | |
| 5,661,133 A | 8/1997 | Leiden et al. | |
| 5,662,124 A | 9/1997 | Wilk | |
| 5,693,029 A | 12/1997 | Leonhardt | |
| 5,698,531 A | 12/1997 | Nabel et al. | |
| 5,700,243 A * | 12/1997 | Narcisco, Jr. | 606/16 |
| 5,733,280 A | 3/1998 | Avitall | |
| 5,797,870 A | 8/1998 | March et al. | |
| 5,797,960 A | 8/1998 | Stevens et al. | |
| 5,820,592 A | 10/1998 | Hammerslag | |
| 5,827,216 A | 10/1998 | Igo et al. | |
| 5,830,993 A | 11/1998 | Blecha et al. | |
| 5,833,658 A | 11/1998 | Levy et al. | |
| 5,840,031 A | 11/1998 | Crowley | |
| 5,840,059 A | 11/1998 | March et al. | |
| 5,840,062 A | 11/1998 | Gumaste et al. | |
| 5,843,050 A | 12/1998 | Jones et al. | |
| 5,846,221 A | 12/1998 | Snoke et al. | |
| 5,857,464 A | 1/1999 | Desai | |
| 5,860,953 A | 1/1999 | Snoke et al. | |
| 5,871,495 A | 2/1999 | Mueller | |
| 5,876,373 A | 3/1999 | Giba et al. | |
| 5,882,332 A | 3/1999 | Wijay | |
| 5,885,272 A | 3/1999 | Aita et al. | |
| 5,891,133 A | 4/1999 | Murphy-Chutorian | |
| 5,661,133 A | 6/1999 | Leiden et al. | |
| 5,931,831 A | 8/1999 | Linder | |
| 5,935,063 A | 8/1999 | Nguyen | |
| 5,941,845 A | 8/1999 | Tu et al. | |
| 5,941,868 A | 8/1999 | Kaplan et al. | |
| 5,964,754 A | 10/1999 | Osypka | |
| 5,971,983 A | 10/1999 | Lesh | |
| 5,993,443 A | 11/1999 | Murphy-Chutorian et al. | |
| 5,997,525 A | 12/1999 | March et al. | |
| 6,004,269 A | 12/1999 | Crowley et al. | |
| 6,012,457 A | 1/2000 | Lesh | |
| 6,024,703 A | 2/2000 | Zanelli et al. | |
| 6,033,645 A * | 3/2000 | Unger et al. | 424/9.5 |
| 6,063,022 A | 5/2000 | Ben-Haim | |
| 6,133,233 A | 10/2000 | Ross et al. | |
| 6,161,543 A | 12/2000 | Cox et al. | |
| 6,171,303 B1 | 1/2001 | Ben-Haim et al. | |
| 6,179,809 B1 | 1/2001 | Khairkhahan et al. | |
| 6,183,444 B1 | 2/2001 | Glines et al. | |
| 6,224,584 B1 | 5/2001 | March et al. | |
| 6,237,605 B1 | 5/2001 | Vaska et al. | |
| 6,309,375 B1 | 10/2001 | Glines et al. | |
| 6,314,962 B1 | 11/2001 | Vaska et al. | |
| 6,314,963 B1 | 11/2001 | Vaska et al. | |
| 6,547,787 B1 * | 4/2003 | Altman et al. | 606/41 |

FOREIGN PATENT DOCUMENTS

| | | |
|---|---|---|
| WO | WO 97/25101 | 7/1997 |
| WO | WO 97/47253 | 12/1997 |
| WO | WO 99/39624 | 8/1999 |
| WO | WO 00/57895 | 10/2000 |

OTHER PUBLICATIONS

Padua et al., "Basic fibroblast growth factor is cardioprotective in ischemia-reperfusion injury" Molecular and Cellular Biochemistry 143: 129-135 (1995).

Shi et al., "PR-39, a proline-rich antibacterial peptide that inhibits phagocyte NADPH oxidase activity by binding to Src homology 3 domains of p47phox" Proc. Natl. Acad. Sci. 93:6014-6018 (1996).

Uchida et al., "Angiogenic therapy of acute myocardial infarction by intrapericardial injection of basic fibroblast growth factor and heparin sulfate: An experimental study" Am. Heart J., 130:1182-1188 (1995).

Unger et al. "Basic fibroblast growth factor enhances myocardial collateral flow in a canine model" Am J. Physiol., 266:H1577-H1595 (1994).

Walterberger et al., "Ischemia-Induced Transplant Arteriosclerosis in the Rat" Arteriosclerosis, Thrombosis and Vascular Biology 16(12):1516-1523 (1996).

Xiaobing, et al. "Ischemia and Reperfusion reduce the Endogenous Basic Fibroblast Growth Factor (bf GF) in Rat Skeletal Muscles" Chinese Medical Journal 108(9): 699-703, (1995).

\* cited by examiner

PHOTOATHEROLYTIC CATHETER APPARATUS AND METHOD

This application claims priority of U.S. Provisional Patent Application No. 60/191,777 filed Mar. 24, 2000, which is incorporated in its entirety herein by reference.

FIELD OF THE INVENTION

The present invention relates to a catheter apparatus for use in photoatherolytic therapy, and a method that uses the apparatus.

BACKGROUND OF THE INVENTION

Transluminal coronary angioplasty was introduced in the late 1970's as a nonsurgical treatment for obstructive coronary artery disease. Since its introduction, major advances in equipment and techniques have led to widespread use of the method for treating coronary artery disease and angina.

In a typical endovascular procedure the treatment device is brought in close proximity to the lesion. Because the diseased vessels are narrowed and often tortuous, the device must be able to navigate through tortuous vasculature and cross through tight lesions. For example, in an angioplasty procedure, typically a balloon catheter is advanced coaxially over a guidewire and forced through the lesion prior to dilation. In photodynamic therapy (PDT), a light source, typically a fiber optic needs to be brought to the lesion site where a photoinitiator compound was selectively taken up. In addition, the light needs to uniformly deliver over a relatively long length (~2 cm) requiring the need of optical diffusers to spread out the light delivered through the fiber or fiber bundle.

Despite improvements in equipment and techniques, restenosis persists as the limiting factor in the maintenance of vessel patency in angioplasty, occurring in 30% to 50% of patients, and accounting for significant morbidity and health care expenditures. Post-angioplasty restenosis is a segmentally limited, wound healing response to a traumatization of the vascular wall.

SUMMARY OF THE INVENTION

In one embodiment, the invention includes a method of treating an atherosclerotic target region of a coronary vessel in a patient. The method includes delivering to the patient, a photoatherolytic compound, to cause accumulation of the compound in the target region. The target region is then accessed intraluminally with a guidewire, followed by placement of a catheter at the target site by advancing over the guidewire, a catheter having (i) a proximal main-body sleeve, (ii) a flexible, non-inflatable, translucent distal-end sleeve joined to the main-body sleeve at a catheter juncture, and (iii) an inner lumen extending through the two sleeves.

After thus positioning the catheter's distal-end sleeve within the target region, the guidewire is removed, and replaced with a fiber-optic bundle having a light-diffusing tip, until the tip is positioned adjacent the catheter juncture. After injecting a light-transmissive fluid, such as a transparent or translucent aqueous solution, through the catheter into the catheter's distal-end sleeve, the target region is irradiated by passing a laser light beam through the fiber optic bundle. The beam is distributed along the catheter's distal-end sleeve, for transmission through the sleeve, by light scattering produced by (i) the light-diffusing tip, (ii) the light-transmissive fluid in the catheter's distal-end sleeve, and/or (iii) the distal sleeve itself. The scattered light is effective to photoactivate a photoatherolytic compund contained in the target region. kradiation is typically carried out for 10–20 minutes.

The photoatherolytic compound may be one currently used in photodynamic therapy, such as a phycocyanin, a phthalocynanine, pheophorbide derivative PH-1126, mono-L-aspartyl chlorin e6 (NPe6), hematoporhyrin derivative (HpD), benzoporphyrin derivative (BPD), Photofrin and Photofrin 2, protoporphyrin IX, and dihematoporphyrin-ester and -ether (DHE).

In one embodiment, the catheter has a wall port distal to catheter juncture, and is positioned downstream of target region in the coronary vessel, when catheter is fully advanced. Using this embodiment allows the user to retract the catheter slightly during operation, to position the port upstream the target, and thereby allow blood in the vessel to flow into wall port and through the distal end region, to promote blood flow through the target region of the vessel at intervals during the treatment procedure.

In another aspect, the invention includes an apparatus for use in treating an atherosclerotic target region of a coronary vessel in a patient. The apparatus includes a guidewire for accessing the target region intraluminally, and a catheter having (i) a proximal main-body sleeve, (ii) a flexible, non-inflatable, translucent distal-end sleeve joined to the main-body sleeve at a catheter juncture, and (iii) an inner lumen extending through the two sleeves, through which lumen the catheter can be advanced over the guidewire, with such positioned in the target region, to place the catheter's distal-end sleeve within the target region.

Also included in the apparatus are (i) a fiber-optic having a light-diffusing tip, the bundle being adapted to be introduced through the catheter lumen, with the catheter's distal-end sleeve placed within the target site, (ii) a proximal-end catheter port through which a light-transmissive fluid can be injected thought the catheter into the catheter's distal-end sleeve, and (iii) a proximal-end optical connector through which the fiber-optic bundle can be connected to a light source, such as a laser, for irradiating the atherosclerotic vessel region by passing, for example, a laser light beam, through the fiber-optic bundle. In operation, a light beam, again for example, a laser light beam, is distributed along the catheter's distal-end sleeve, for transmission through the sleeve, by light scattering produced by (i) the light-diffusing tip, (ii) the light-transmissive fluid injected into the catheter's distal-end sleeve and/or (iii) the distal sleeve itself.

The catheter has a preferred inner-lumen diameter of between about 0.45 mm and 0.6 mm. The optic fiber bundle is preferably formed of a plurality of light fibers encased in an outer sleeve for relative axial fiber sliding movement, to enhance the flexibility of the fiber bundle, and the catheter preferably has a wall port upstream of the juncture, located to allow blood in the patient's vessel to flow into and through said distal end sleeve, with the catheter distal-end sleeve placed in the target region, and withdrawn to place the port just upstream of the target region.

In summary, this invention enables efficient navigation through tortuous vasculature and superior crossing ability of tight lesions. It also enables efficient delivery of light energy to the lesion by combining the light emitting quality of a fiber or bundle with the diffusive properties of an outer sheath to deliver light uniformly over the region. Finally, this invention enables protection against abrupt reclosure by maintaining a lumen across the lesion during the PDT procedure.

These and other objects and features of the present invention will become more fully apparent when the following detailed description of the invention is read in conjunction with the accompanying drawings.

DETAILED DESCRIPTION OF THE INVENTION

The apparatus of the invention comprises: 1) a low profile over-the-wire catheter that incorporates an optically translucent or transparent distal section and a stiffer, more pushable proximal section, 2) a fiber optic bundle that is advanced through the catheter until the light emitting end of the bundle reaches the transparent catheter section, 3) light generation means connected to the proximal end of the fiber, 4) a fluid that fills the internal lumen of the catheter that transmits light energy over a length.

Figure 1:
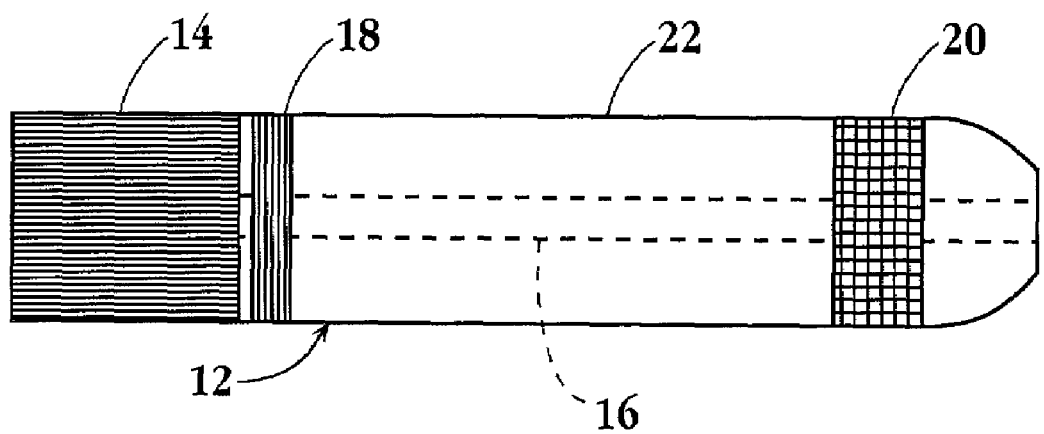
FIG. 1 shows the distal-end portion of an apparatus constructed in accordance with the invention.
Figure 2:
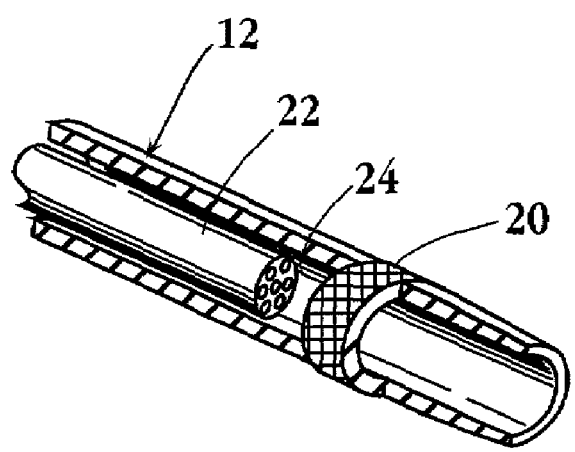
FIG. 2 is a cutaway view of the distal-end portion shown in FIG. 1.

FIGS. 1 and 2 show a distal-end portion of the apparatus, indicated at 12, showing the distal-end portion of a catheter jacket 14, a distal-end diffuser 16, and a juncture 18 between the two. The distal-end diffuser may be transparent or translucent, providing either a transparent light sleeve or a light-scattering sleeve. This distal section of the catheter is made from an optically transparent, heat stable, flexible material, such as a crosslinked polymer, for example polyethylene or polytetrafluroroethylene (PTFE). The flexibility allows the catheter to track easily over the wire, the transparentcy allows light to escape through the wall, and heat stability prevents heat deformation from the light energy. Light scattering particles may be added to the sleeve material.

A portion of the diffuser is bounded by radio-opaque bands 20. A bundle of light fibers 22 (see also FIG. 2) is axially positionable within the inner lumen of the catheter. The fiber bundle is preferably encased in a flexible sleeve, without any attachment between fibers, allowing the individual fibers to slide somewhat relative to the bundle mass, thus providing greater flexibility in maneuvering the bundle through the catheter.

In one embodiment, the fiber optic bundle is made from a plurality, e.g., 7, plastic fibers, 100 micron diameter each in a geometrically stable configuration, held together by an outer jacket that provides flexibility distally and pushability proximally. The proximal section may incorporate a polyimide jacket, the distal section may be made from a flexible material, such as polyethylene. A light diffuser may be incorporated at the distal end of the bundle. Typical diffuser manufacture techniques are well known and may include surrounding a portion of the exposed individual fibers with a scattering material such as barium sulfate.

Figure 5:
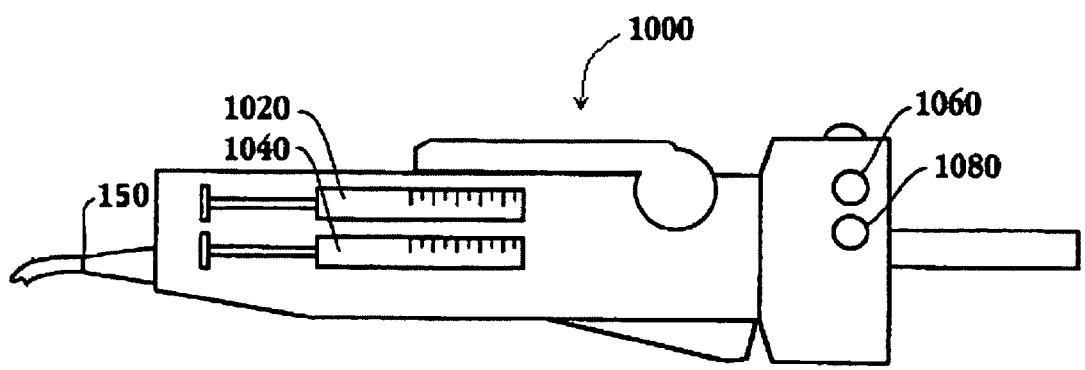
FIGS. 5 shows details of a control handle in an apparatus constructed according to another embodiment of the invention.

The space downstream of the fiber bundle defines an optical space 24 that may be filled with a clear or translucent aqueous solution supplied through the catheter from the proximal end thereof through proximal end catheter port 150 see FIG. 5).

In one embodiment, where the light bundle is placed within the target region in the catheter, i.e., within optical space 24, the sleeve encasing the distal-end region of the bundle is either transparent or optionally, translucent, providing a light diffuser on the bundle, as noted above. In this embodiment, light diffusion in the target region is effected by at least one of the following (i) the distal end region of the catheter; (ii) the sleeve encasing the distal end of the light bundle, and (iii) fluid, e.g., aqueous medium injected into the distal end region of the catheter.

In another embodiment, the light bundle is placed just upstream of the target region, i.e., upstream of optical space 24. Here only the distal ends of the fibers need to be open to light transmission. In this embodiment, light from the bundle is diffused into the distal end region of the catheter by the distal end region of the catheter and/or fluid injected into the distal end region of the catheter.

FIGS. 3A–3D show the positioning of a distal end portion of the apparatus within a chamber of a heart 26, for accessing a vascular target region of the heart in need of phototherapy. Initially, although not shown, the patient is administered a photosensitizing compound, typically by systemic administration, and the compound is allowed to accumulate at the target site, according to known phototherapy principles.

Exemplary photosensitizing compounds are those used in phototherapy, such as a phycocyanin, a phthalocynanine, pheophorbide derivative PH-1126, mono-L-aspartyl chlorin e6 (NPe6), hematoporhyrin derivative (HpD), benzoporphyrin derivative (BPD), Photofrmn and Photofrin 2, protoporphyrin IX, and dihematoporphyrin -ester and -ether (DHE).

Figure 3A:
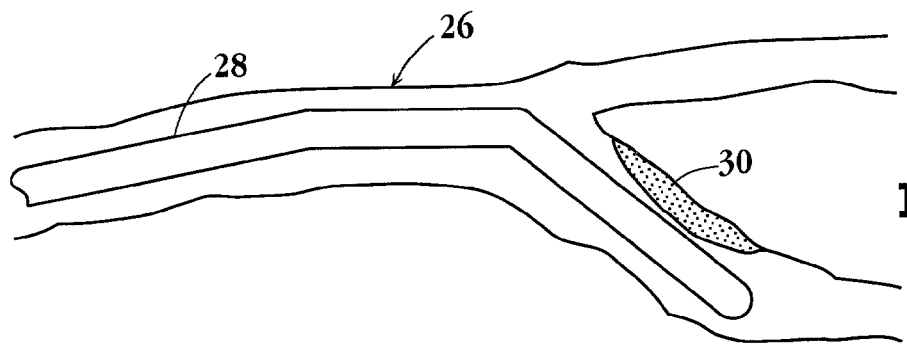
FIGS. 3A–3D show steps in practicing the phototherapy method of the invention, using the apparatus of the invention.

Following this, a conventional guidewire 28 is advanced through the vasculature, such as vasculature to the target site 30 composed an atherosclerotic plaque. The guidewire is advanced through the target region, as shown in FIG. 3A, to position the end of the guidewire downstream of the target site.

The conventional guidewire is typically 0.014" diameter in coronary applications. The inner lumen of the catheter is large enough to permit advancement and flushing around the guidewire, approximately 0.018" and larger. The outer diameter of the catheter is minimized for superior low profile, about 0.030" (including a radio-opaque marker).

Figure 3B:
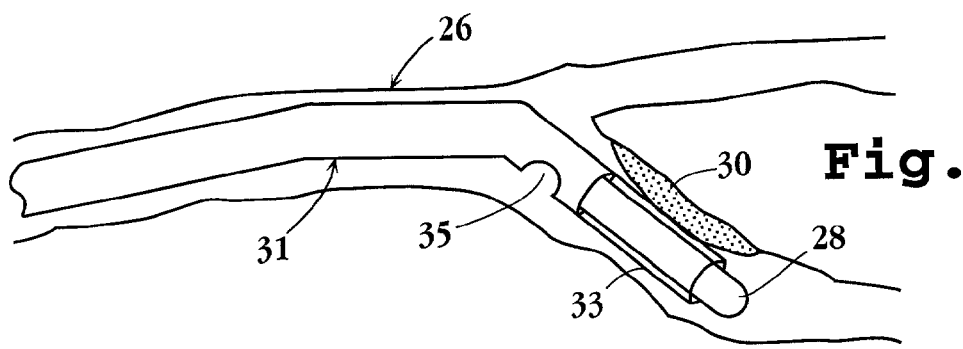
Figure 3C:
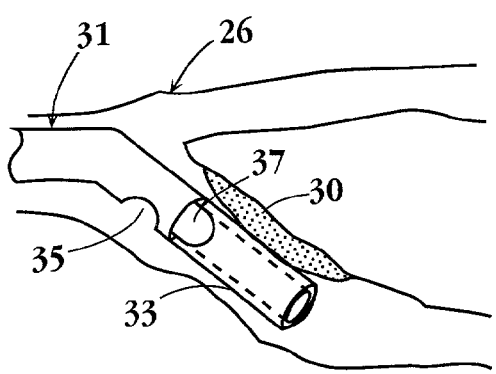

With the guidewire so placed, the catheter, such as catheter 31 similar to that described above, is advanced over the guidewire, so as to position the distal-end diffuser, shown at 33, in the catheter within the target site, as illustrated in FIG. 3B. An advantage of the method, to this point, is that the more flexible and smaller diameter guidewire can act as a guide for moving the distal end of the catheter within the somewhat occluded target site.

With the catheter so positioned, the guidewire is removed from the catheter and replaced with a fiber bundle 37 that is advanced through the catheter lumen to place the end of the fiber bundle either upstream of the distal-end space corresponding to the target region (FIG. 3C), or within this space (FIG. 3D), as noted above. Following this placement, aqueous liquid, such as saline solution or ionic contrast, is forced through the catheter lumen from the catheter's proximal end, to either fill the distal-end optical space of the catheter with a clear or translucent fluid for the method illustrated in FIG.

Figure 3D:
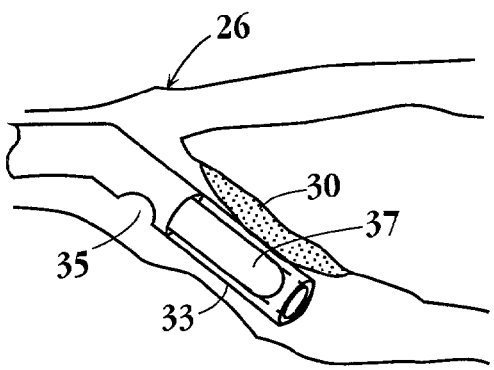

3C, or to fill the annulus between the fiber bundle and catheter distal end with fluid, as in the method illustrated in FIG. 3D.

The proximal end of the light bundle is then coupled to a laser or other suitable light source in the apparatus, for directing a light beam into the optical space of the catheter. The selected light wavelength will depend on the photosensitizer administered, which can be determined from a variety of literature sources on photodynamic therapy.

In tight lesions, the catheter acts to support the guidewire and allows greater pushability and greater crossing ability than the guidewire acting alone. The catheter may also be provided with a side-wall port 35 just upstream of the diffuser, to allow for blood flow through the distal end region of the catheter and across the partially blocked plaque area during a phototherapy operation. This is accomplished by periodically retracting light bundle 37 to a point just upstream of the port, allowing blood to flow through the distal end of the catheter, across the lesion. Typically, the phototherapy will be carried out continuously, or with periodic irradiation for a period of total light irradiation of about 10–20 minutes. The power of the optical source can be adjusted, depending on the efficiency of light transmission from the optical space to the surrounding target tissue, to achieve a desired photo-intensity at the target region. These variables again can be determined from published studies on phototherapy efficacy at various light-intensities and photosensitizer concentrations. As indicated above, the total irradiation time may be periodically interrupted to allow blood flow across the lesion, without having to reposition catheter within the target area.

Figure 4A:
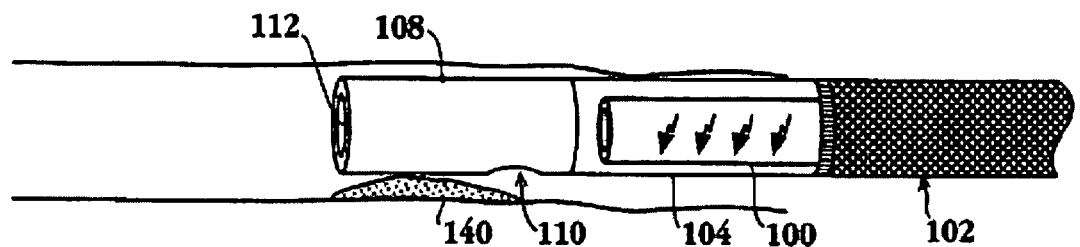
FIGS. 4A and 4B represent additional features of practicing the method of the invention.
Figure 4B:
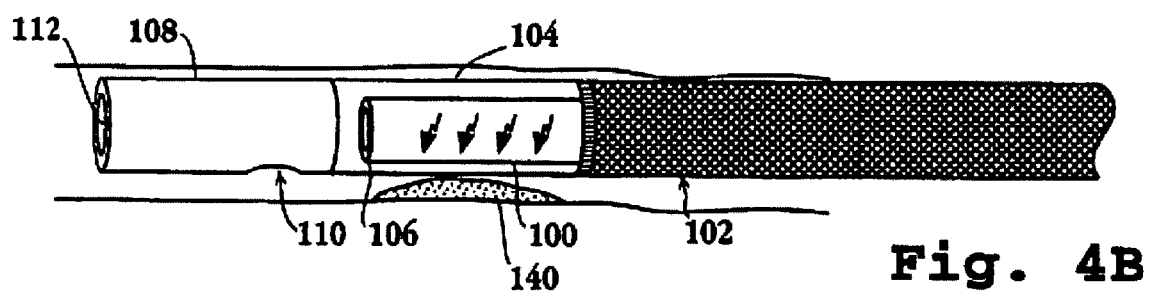

FIGS. 4A and 4B illustrate an alternative approach for allowing periodic blood across a partially blocked lesion 110 attached to the downstream end of the catheter's diffuser 108. In operation, this segment is initially positioned downstream of the target lesion, indicated at 140, in the coronary vessel, so as to place the transparent of translucent diffuser 104 in the catheter adjacent the target region. This embodiment allows the user to retract the catheter slightly during a light-therapy procedure, as depicted in FIG. 4A, to position the port upstream of the target, and thereby allow blood in said vessel to flow into wall port (110) and through said distal end region, exiting at end of the catheter lumen (112), to promote blood flow through the target region of the vessel at intervals during the treatment procedure. During actual phototherapy, the catheter is advanced slightly, as in FIG. 4B, to place the transparent or translucent portion 104 and a light fiber or fiber bundle 100 is positioned for light-delivery to the target area. During the procedure, the catheter may be periodically retracted, to allow blood flow across the target area, as in FIG. 4A, and extended for irradiating the area, as in FIG. 4B, without having to breach the plaque area, i.e., without having to advance the catheter across the partially constricted plaque region each time the catheter is retracted to allow for blood flow across the area.

Another embodiment of the invention provides the catheter as described above, but having a proximal end user control handle 1000 depicted in FIG. 5. Handle 1000 allows for intermittent injections of contrast agent to check flow in the target region. Specifically, the handle allows for switching between delivering or flowing transparent solution contained in syringe 1020 and contrast solution contained in syringe 1040. Indicator lights 1060 and (1080) provide the user with information about the adequacy of the flow of either solution by indicating either a "good" or "compromised" flow. The indicator lights are activated by a flow sensor, not shown, situated, for example, at the distal end of the catheter. The flow sensor monitors flow during a procedure. In another embodiment, contrast and aqueous solution injection can be alternated automatically by employing a timer and switching device integrated into the handle, thus creating a "smart handle", or as an alternative for example, a switching device situated externally from the handle.

Figure 6A:
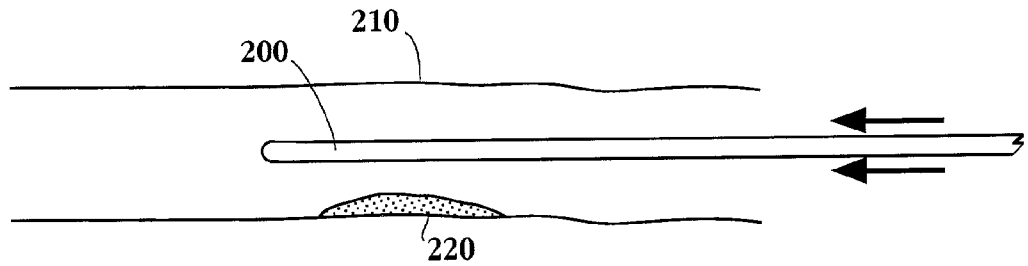
FIGS. 6A–6J illustrate steps in practicing the method of the invention.
Figure 6B:
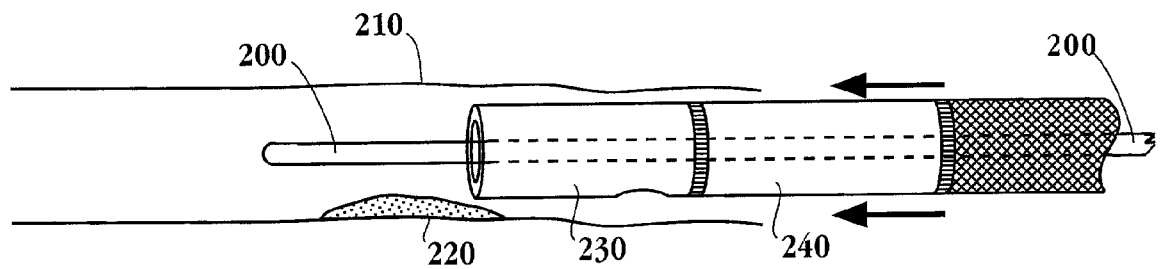
Figure 6C:
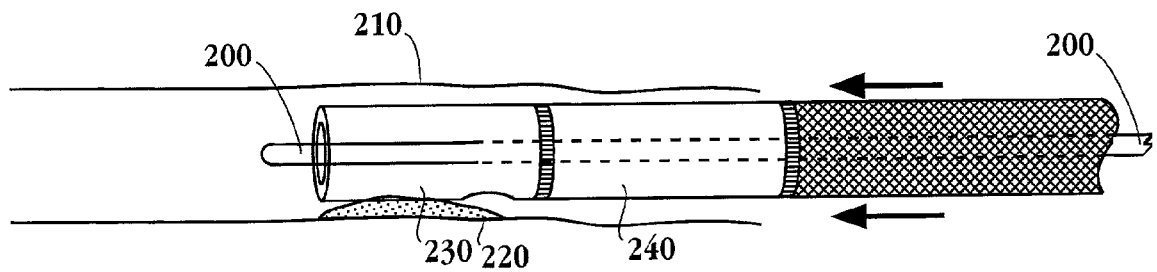
Figure 6D:
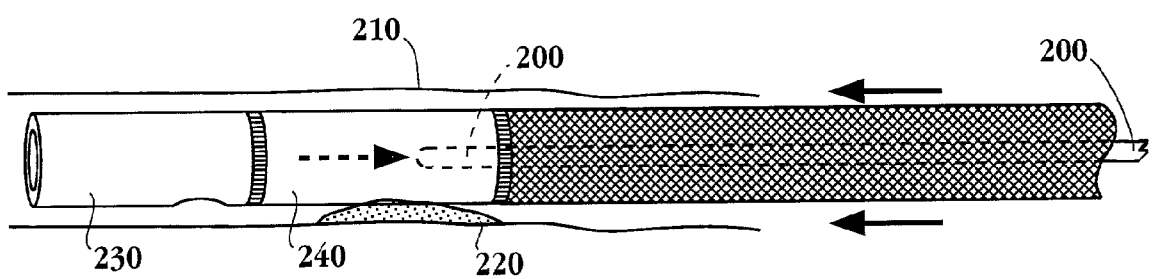
Figure 6E:
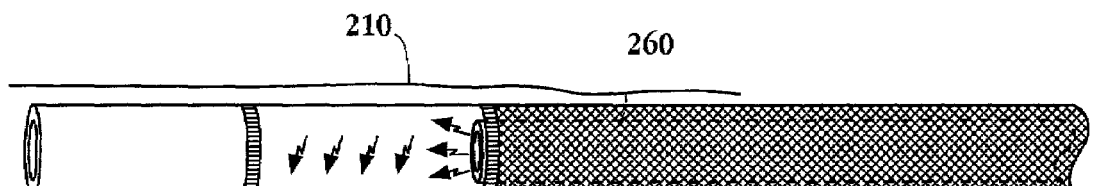
Figure 6F:
Figure 6G:
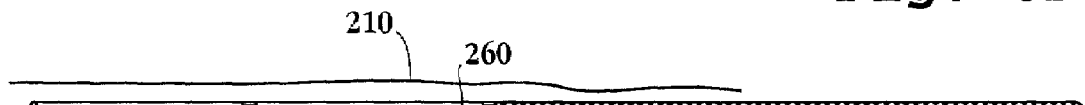

FIGS. 6A–6J illustrate various steps in the operation of the apparatus, and method of the invention. Initially, a guidewire 200 is inserted through lumen 210 of a patient vessel and guided to target region 220 (FIG. 6A). A catheter 230, with its illumination or diffuser segment 240 and end segment 250 is introduced over guidewire 200 and urged forward along the guidewire (FIG. 6B) to move the catheter end segment through the partially blocked target region, as shown in FIG. 6C. Here, catheter 230 works in concert with guidewire 200 to breach the partially blocked target region with the end of the catheter. Once the end segment is pushed beyond the target region, the catheter is further urged forward to position the diffuser adjacent the target region (FIG. 6D). At this point, the guidewire is withdrawn from the catheter and replaced with light fiber or conductor 260 which is guided through catheter 230 toward the target region, as shown in FIG. 6E. Specifically, the end of light fiber 260 is urged forward until it either traverses and occupies the lumen area of the diffuser, as in FIG. 6G, or in the case where a photoconductive fluid is introduced into the diffuser lumen via the catheter, the light fiber 260 is urged to a position just upstream of the diffuser, as shown in FIG. 6F.

Figure 6H:
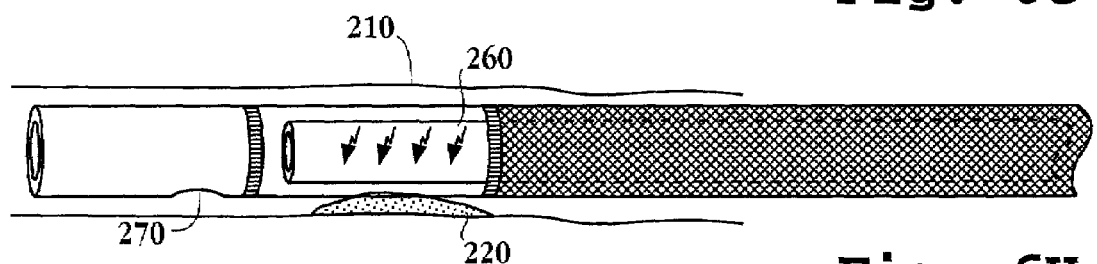
Figure 6I:
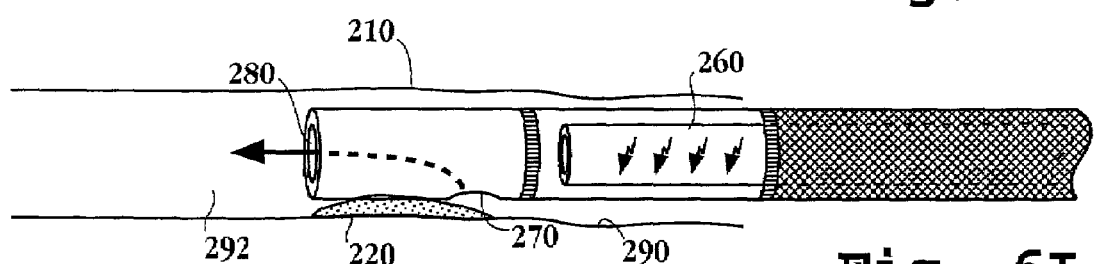
Figure 6J:
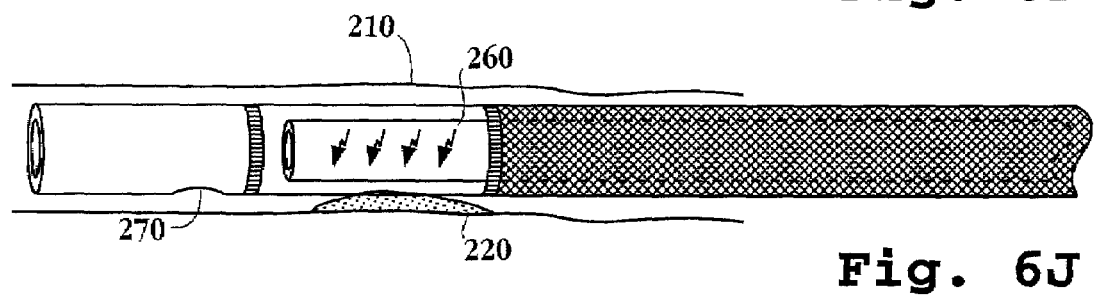

To initiate phototherapy, a light source, such a laser beam of a selected wavelength, is applied to the end of the light fiber 260, to illuminate the region at the end of the light bundle, or at the end region, if the light bundle is exposed along its distal end region, corresponding to the diffuser length. This will provide illumination to the target area, either via light dispersion in the diffuser fluid by light dispersing agents or particles in the fluid introduced into the diffuser, as shown in FIG. 6F, or direct illumination from the exposed distal tip region of the light bundle as seen in FIG. 6H.

Where the catheter diameter is such as to effectively block blood flow in the target vessel, the user may elect to provide blood supply to the downstream region of the target vessel by slightly withdrawing the catheter away from target region, to place the end segment of the catheter adjacent the region, as shown in FIG. 6i. In this position, blood flow is achieved because the occlusion formed by the catheter is temporarily breached by a fluid pathway between a sidewall orifice 270 and the open end of the end segment. After a period sufficient to oxygenate the downstream portion of the vessel, the catheter may be advance back to its illumination position for further light treatment (FIG. 6J), and this alternate illuminating, oxygenating is continued until a desired total illumination time is achieved.

The invention provides several advantages for photodynamic therapy methods known in the prior art, such as Balloon Dilation Catheters, Over-the-Wire Catheters with fibers integrated in the wall, and Diffusing Guidewires.

(i). The crossing profile of the apparatus of the invention is much lower than a balloon dilation catheter; and in addition, the ability to navigate in tortuous anatomy is not hindered by a balloon that adds stiffness to the distal end. PDT procedures take up to 15 minutes to deliver energy so the least traumatic system that minimizes vessel injury is preferred.

(ii). The current invention utilizes conventional manufacturing techniques making the components relatively easy to manufacture, in contrast to fibers integrated into the catheter wall, that again hinder navigation properties due to their stiffness.

(iii) The present invention takes advantage of the liquid inside the lumen to increase the effective area of energy delivery in contrast to a diffusing guidewire whose cross section is relatively small in order to achieve the flexibility necessary to navigate in tortuous anatomy.

(iv) The light delivery and diffusing ability of the system can be shared among three components: The fiber bundle, the catheter and the fluid used through the catheter during the procedure.

(v) The use of a catheter that crosses the lesion allows for removal and reintroduction of the guidewire without losing position across the lesion.

(vi) Since the navigation component (catheter) and optical transport component (the bundle) can be optimized for their function without the compromises brought in by integrating the second function into one device, the light diffusion component is shared synergistically between components.

(vii) The catheter and guidewire act synergistically to cross tight lesions.

These advantages depend on the novel features of the invention described above, including:

Synergistic delivery of diffuse light energy over a region of interest by combining a fiber bundle, a catheter with translucent or transparent section and a flushing fluid with favorable optical properties for light transmission.

Low profile, pushable components with flexible distal portions to facilitate navigation, crossing of tight lesions and light delivery with low level of obstruction and irritation during an extended procedure. Components do not require modification of standard interventional procedures.

Although the invention has been described with reference to a particular embodiment, it will be appreciated that various and changes and modifications may be made without departing from the spirit of the invention.

The invention claimed is:

1. Apparatus for use in treating an atherosclerotic target region of a coronary vessel in a patient, comprising
   a guidewire for accessing the target region intraluminally,
   a catheter having (i) a proximal main-body sleeve associated with a handle, (ii) a flexible, non-inflatable, translucent distal-end sleeve joined to the main-body sleeve at a catheter juncture, and (iii) an inner lumen extending through the two sleeves, through which lumen the catheter can be advanced over the guidewire to position the catheter's distal-end sleeve within the target region,
   a fiber-optic bundle having a light-diffusing tip, said bundle being adapted for introduction into and slidably associated with the catheter lumen after the catheter's distal-end sleeve is positioned within the target region, and the guidewire is removed;
   a proximal-end catheter port through which a light-transmissive fluid can be injected through the catheter into the catheter's distal-end sleeve, and
   a proximal-end optical connector to which the fiber-optic bundle can be connected to a laser source, for irradiating the atherosclerotic target region by passing a laser light beam through the fiber optic bundle,
   such that the laser beam is distributed along the catheter's distal-end sleeve, for transmission through the sleeve, by light scattering produced by (i) the light-diffusing tip, (ii) the light-transmissive fluid injected into the catheter's distal-end sleeve and (iii) the distal-end sleeve, and where the scattered light transmitted through the sleeve is effective to photoactivate a photoatherolytic compound contained in the target region; and
   wherein the handle comprises a first syringe containing a light-transmissive fluid and a second syringe containing a contrast fluid;
   wherein the handle further comprises first and second indicator lights configured to indicate the flow of the light-transmissive fluid and the contrast fluid;
   wherein the catheter further comprises a sensor, and
   wherein the sensor is configured to activate the first and second indicator lights.

2. The apparatus of claim 1, wherein the sensor is located at the distal end of the catheter.

3. The apparatus of claim 1, wherein the handle permits for intermittent injections of both the light-transmissive fluid and the contrast fluid.

4. The apparatus of claim 3, wherein the handle further comprises a timer and a switching device configured to automatically inject the light-transmissive fluid and contrast fluid.

* * * * *